United States Patent
Lee et al.

(10) Patent No.: US 9,554,117 B2
(45) Date of Patent: Jan. 24, 2017

(54) SYSTEM AND METHOD FOR NON-INVASIVE PATIENT-IMAGE REGISTRATION

(71) Applicant: KOREA INSTITUTE OF SCIENCE AND TECHNOLOGY, Seoul (KR)

(72) Inventors: Deukhee Lee, Seoul (KR); Se Hyung Park, Seoul (KR); Sunghwan Lim, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 257 days.

(21) Appl. No.: 14/077,462

(22) Filed: Nov. 12, 2013

(65) Prior Publication Data

US 2015/0049174 A1     Feb. 19, 2015

(30) Foreign Application Priority Data

Aug. 13, 2013 (KR) .......................... 10-2013-0096016

(51) Int. Cl.
    *H04N 13/02*     (2006.01)
    *G06T 7/00*     (2006.01)
    (Continued)

(52) U.S. Cl.
    CPC ......... *H04N 13/0221* (2013.01); *A61B 90/361* (2016.02); *G06T 7/0028* (2013.01);
    (Continued)

(58) Field of Classification Search
    CPC ....... A61B 19/52; A61B 6/504; A61B 8/0891; G06T 2207/10012; G06T 2207/10048; G06T 2207/10072; G06T 2207/20044; G06T 2207/30101; G06T 2207/30172; G06T 7/0028; H04N 13/0221
    (Continued)

(56) References Cited

U.S. PATENT DOCUMENTS 7,826,889 B2 * 11/2010 David ................ A61B 19/5244
                                                                                 600/3
8,374,410 B2 * 2/2013 Ohyu ..................... A61B 6/463
                                                                                382/128

(Continued)

FOREIGN PATENT DOCUMENTS

FR    WO 2012117381 A1 * 9/2012 ............. A61B 19/52
KR    10-2013-0045774 A     5/2013

OTHER PUBLICATIONS

Kandani et al., Development of blood vessel searching system for HMS, Aug. 27, 2008, Infrared Systems and Photoelectronic Technology III Proc. SPIE 7055.*

*Primary Examiner* — Francis G Geroleo
(74) *Attorney, Agent, or Firm* — NSIP Law

(57) ABSTRACT

A system for non-invasive registration between a patient and a three-dimensional (3D) medical image includes a near infrared 3D camera 110 which extracts a 3D blood vessel image I2 of a patients registration target area during surgical operation; a camera position tracer 120 which traces a position of the near infrared 3D camera 110 and calculates a real world coordinate system of the 3D blood vessel image I2; a controller 130 which extracts a first blood vessel pattern from a 3D medical image I1 of the registration target area, extracts a second blood vessel pattern from the 3D blood vessel image I2, and performs position registration between the patient and the 3D medical image I1 through the extracted first and second blood vessel patterns; and a display 140 which displays a registration result calculated by the controller 130.

7 Claims, 7 Drawing Sheets

(51) Int. Cl.
*A61B 6/00* (2006.01)
*A61B 8/08* (2006.01)

(52) U.S. Cl.
CPC ............ *A61B 6/504* (2013.01); *A61B 8/0891* (2013.01); *A61B 2034/2055* (2016.02); *A61B 2090/364* (2016.02); *G06T 2207/10012* (2013.01); *G06T 2207/10048* (2013.01); *G06T 2207/10072* (2013.01); *G06T 2207/20044* (2013.01); *G06T 2207/30101* (2013.01); *G06T 2207/30172* (2013.01)

(58) Field of Classification Search
USPC .......................................................... 348/50
See application file for complete search history.

(56) References Cited

U.S. PATENT DOCUMENTS

| | | | | |
|---|---|---|---|---|
| 8,463,006 B2* | 6/2013 | Prokoski | ............. | A61B 5/0064 382/128 |
| 8,463,360 B2* | 6/2013 | Yamamoto | ................... | 600/407 |
| 2003/0000535 A1* | 1/2003 | Galloway, Jr. | ......... | A61B 19/52 128/898 |
| 2003/0053697 A1* | 3/2003 | Aylward | ............... | G06T 7/0012 382/203 |
| 2008/0144773 A1* | 6/2008 | Bar-Zohar | ......... | A61B 1/00096 378/98.12 |
| 2008/0317321 A1* | 12/2008 | Zhang | .................... | G06T 15/08 382/132 |
| 2009/0005668 A1* | 1/2009 | West | ...................... | A61B 6/466 600/407 |
| 2010/0098299 A1* | 4/2010 | Muquit | .............. | G06K 9/00013 382/115 |
| 2010/0172567 A1* | 7/2010 | Prokoski | ............. | A61B 5/0064 382/132 |
| 2011/0158487 A1* | 6/2011 | Ohyu | ..................... | A61B 6/463 382/128 |
| 2012/0215094 A1* | 8/2012 | Rahimian | ........... | A61B 1/00193 600/414 |
| 2014/0005527 A1* | 1/2014 | Nagarkar | ................. | A61B 5/05 600/424 |
| 2014/0072196 A1* | 3/2014 | Hwang | ................. | G06T 7/0016 382/130 |
| 2014/0148690 A1* | 5/2014 | Kim | ...................... | G06T 7/0038 600/424 |
| 2014/0193053 A1* | 7/2014 | Kadoury | ............. | A61B 19/52 382/131 |
| 2014/0218720 A1* | 8/2014 | Kindem | ............... | A61B 6/4258 356/72 |

* cited by examiner (a)

(b)

SYSTEM AND METHOD FOR NON-INVASIVE PATIENT-IMAGE REGISTRATION

CROSS-REFERENCE TO RELATED APPLICATION

This application claims priority from Korean Patent Application No. 10-2013-0096016, filed on Aug. 13, 2013 in the Korean Intellectual Property Office, the disclosure of which is incorporated herein by reference.

BACKGROUND

Field

Apparatuses and methods consistent with the exemplary embodiments relate to a system and method for non-invasive registration between a patient and a patient's three-dimensional (3D) image for registration of a position and a pose between a patient and a patient's 3D medical image, and more particularly to a system and method for non-invasive registration between a patient and a patient's three-dimensional (3D) image, which can align a patient's 3D medical image with a patient by a non-invasive method using a feature point based on a blood vessel pattern, where a patient's blood vessel is extended, without using an artificial fiducial marker.

Description of the Related Art

In general, a minimally invasive surgery is a surgery method that 3~4 small holes are pierced through a skin and an endoscope and a narrow and long surgical instrument are put into the holes so as to minimize skin incision. Such a minimally invasive surgery has been annually increased due to less pain and short recovery time along with minimal scar left when compared to general surgery.

However, in the minimally invasive surgery, an operating surgeon cannot directly see an affected area and therefore indirectly checks an image gained from the endoscope through a monitor. At this time, it is not easy to observe a targeted affected area because a view direction of the surgeon is different from a direction of the endoscope and the endoscope is short-sighted. Further, it is unintuitive and thus difficult to treat the affected area by controlling a surgical instrument while watching an image from the endoscope.

Meanwhile, a non-invasive surgery is a surgery method that ultrasonic waves, radiation, magnetic field, etc. are used for treatment without skin incision. In this surgery method, an operating surgeon cannot directly see an affected area and also cannot use the image from the endoscope in real time. Therefore, surgery navigation has been required to guide the surgical operation of the operating surgeon during an operation through a three-dimensional (3D) medical image (computer tomography (CT), a magnetic resonance imaging (MRI), etc.) of a patient taken for a diagnosis and a surgical plan before the operation.

For the surgery navigation, a patient's 3D medical image has to be first aligned with an intraoperative patient with respect to coordinates. That is, if coordinate transformation between a medical image coordinate system of the 3D medical image and a patient coordinate system (i.e., a coordinate system arbitrarily set up in the real world) is known, it is possible to determine what position of a patient a certain position on the medical image corresponds to. This is called patient-image registration.

As a method generally used for the patient-image registration, there is a method of performing the patient-image registration by taking a medical image in the state that fiducial markers are attached to a patient, and aligning the fiducial markers from previously taken medical image with the fiducial markers that is attached to the patient.

In the case of using the fiducial marker, there are an invasive method of fixing the fiducial markers to a patient's bone, and a non-invasive method of attaching the fiducial marker on a patient's skin. The invasive method burdens a patient due to scar on bone even though registration is relatively precise. On the other hand, the non-invasive method is not applicable to microsurgical operation due to low precision.

Accordingly, a markerless patient-image registration method without using the fiducial markers has recently been researched, in which 3D medical image registration is performed using a patient's two dimensional (2D) sectional image based on ultrasonic waves or X-rays, or using a 3D scan model of a patient's skin surface.

However, the registration between the 2D sectional image and the 3D medical image needs long calculation time and is vulnerable to soft tissue transformation of a human body. Also, the registration between the 3D scan model of a patient's skin surface and a skin surface model extracted from the 3D medical image may have a large error due to change in shape of the skin surface.

Consequently, patient-image registration method which does not use the fiducial markers and is minimally affected by change in a patient's soft tissue and a skin surface are required.

REFERENCES

Patent Reference

KR Laid-Open No. 10-2013-0045774 (KR Application No. 10-2011-0110189)

SUMMARY

The present invention is conceived to solve the foregoing problems, and an aspect thereof provides a system and method for non-invasive registration between a patient and a 3D medical image, which can perform position registration between a 3D image of a blood vessel located in the patient's target registration area, taken using near infrared light penetrating a skin of a human body and having a wavelength largely absorbed in the blood vessel, and a 3D medical image such as magnetic resonance imaging (MRI), computer tomography (CT), etc.

According to an aspect of another exemplary embodiment, a system for non-invasive registration between a patient and a three-dimensional (3D) medical image is provided including: a near infrared 3D camera 110 which extracts a 3D blood vessel image I2 of a patient's registration target area at a surgical operation; a camera position tracer 120 which traces a position of the near infrared 3D camera 110 and calculates a real world coordinate system of the 3D blood vessel image I2; a controller 130 which extracts a first blood vessel pattern from a 3D medical image I1 of the registration target area, extracts a second blood vessel pattern from the 3D blood vessel image I2, and performs position registration between the patient and the 3D medical image I1 through the extracted first and second blood vessel patterns; and a display 140 which displays a registration result calculated by the controller 130.

The controller 130 may comprise a 3D medical image database (DB) 131 which stores a 3D medical image I1 obtained by taking the registration target area before a surgical operation; a blood vessel model generator 132 which reconstitutes the blood vessel model with a blood vessel image separated from the 3D medical image I1; a first feature point extractor 133 which extracts a branch point, from which a blood vessel is branched, by detecting a skeleton line SL of the blood vessel model, and selects each extracted branch point as a feature point of the first blood vessel pattern; a 3D blood vessel image detector 134 which extracts a 3D blood vessel image I2 by separating a blood vessel image from a near infrared 3D image taken by the near infrared 3D camera 110, and a the second feature point extractor 135 which extracts a branch point of a patient's blood vessel at a surgical operation through the extracted 3D blood vessel image I2 and a real world coordinate system of the 3D blood vessel image I2 measured by the camera position tracer 120, and selects each extracted branch point as a feature point of the second blood vessel pattern; and a registrator 136 which performs registration by optimally matching a first feature point group P1 grouping a plurality of first feature points, and a second feature point group P2 grouping a plurality of second feature points.

The first feature point extractor 133 may store 3D coordinates of a feature point of a first blood vessel pattern selected with respect to a medical image coordinate system, the near infrared 3D camera 110 may take blood vessel images seen by having near infrared light pass through a patient's registration target area to obtain two 3D blood vessel images I2 that are spaced apart at a predetermined distance to have parallax, and the second feature point extractor 135 may select a second feature point represented by 3D coordinates with respect to a 3D camera coordinate system, using parallax of a pair of corresponding branch points respectively calculated from two 3D blood vessel images I2 of the near infrared 3D camera 110.

The camera position tracer 120 may measure six degrees of freedom in position of the near infrared 3D camera 110, which includes three rotation positions and three translation positions, and calculates a coordinate transformation matrix M from the position tracer coordinate system to the 3D camera coordinate system by tracing the position of the near infrared 3D camera 110 in real time; the second feature point extractor 135 may transform and save the second feature point in the 3D camera coordinate system into that in a position tracer coordinate system by the coordinate transformation matrix M; and the registrator 136 may calculate a position relationship T of a position tracer coordinate system with respect to a medical image coordinate system in a state that a second feature point group P2 in the position tracer coordinate system is rotated and translated to be optimally matched with the first feature point group P1.

The camera position tracer 120 may comprise a mechanical position tracing device 120a which is fastened to an end of an articulated link and measures six degrees of freedom in position of the near infrared 3D camera 110 by sensing a physical displacement due to link work of each joint.

The camera position tracer 120 may comprise an optical position tracing device 120b which uses a 3D camera taking fiducial markers 121 mounted on the near infrared 3D camera 110 to calculate a 3D position vector and a 3D direction vector of the fiducial marker 121 and measure six degrees of freedom in position of the near infrared 3D camera 110.

The first feature point extractor 133 may extract a border line BL representing an outline of a blood vessel from the blood vessel model, and extract a center line, which is extended from the extracted border line BL along the blood vessel, as a skeleton line SL;

According to an aspect of another exemplary embodiment, a method of non-invasive registration between a patient and a three-dimensional (3D) medical image is provided including: extracting a 3D blood vessel image I2 by taking a blood vessel image seen by having near infrared light pass through a registration target area with a near infrared 3D camera 110 (S210); tracing a camera position by tracing a position of the near infrared 3D camera 110 in real time with the camera position tracer 120 and calculating a real world coordinate system of the 3D blood vessel image I2 (S220); extracting a blood vessel pattern with a controller 130 by extracting a first blood vessel pattern from a 3D medical image I1 of the registration target area and extracting a second blood vessel pattern from the 3D blood vessel image I2 (S230); image registration by performing position registration between a patient and the 3D medical image I1 through the extracted first and second blood vessel patterns (S240); and displaying a registration result by displaying the registration result calculated by the controller 130 on a screen (S250).

In accordance with the system and method for the non-invasive registration between a patient and the 3D medical image, it has the following effects:

First, it is possible to non-invasively perform the registration between the patient and the 3D medical image I1 through the position registration between the 3D blood vessel image I2 of the blood vessel arranged in the patient's registration target area obtained using the near infrared light and the blood vessel model included in the 3D medical image I1 obtained by taking the registration target area, without using any fiducial markers.

Second, each blood vessel pattern of the blood vessel images reconstituted from the 3D blood vessel image I2 and the 3D medical image I1 obtained using the near infrared light is analyzed to calculate the feature point for the registration of the branch point of the blood vessel, and thus the registration is performed with respect to the calculated feature point, thereby not only minimize effect on skin deformation but also reducing an error at the position registration as compared with the conventional registration method using the feature point on a patient's skin.

Third, the position registration is performed based on the feature point according to the blood vessel pattern extended from the blood vessel distributed throughout a human body, thereby being advantageously applicable to various surgical areas and usable as medical information in connection with various medical images.

Fourth, while the feature point of the blood vessel pattern is extracted from the 3D blood vessel image and the 3D medical image, a center line extended along the blood vessel displayed in each image is extracted as a skeleton line, and the branch point of each skeleton line is selected as the feature point, thereby minimizing an error about a border line of the blood vessel and further reducing the registration error.

BRIEF DESCRIPTION OF THE DRAWINGS

The above and/or other aspects will become apparent and more readily appreciated from the following description of exemplary embodiments, taken in conjunction with the accompanying drawings, in which.

DETAILED DESCRIPTION OF EXEMPLARY EMBODIMENTS

Figure 1:
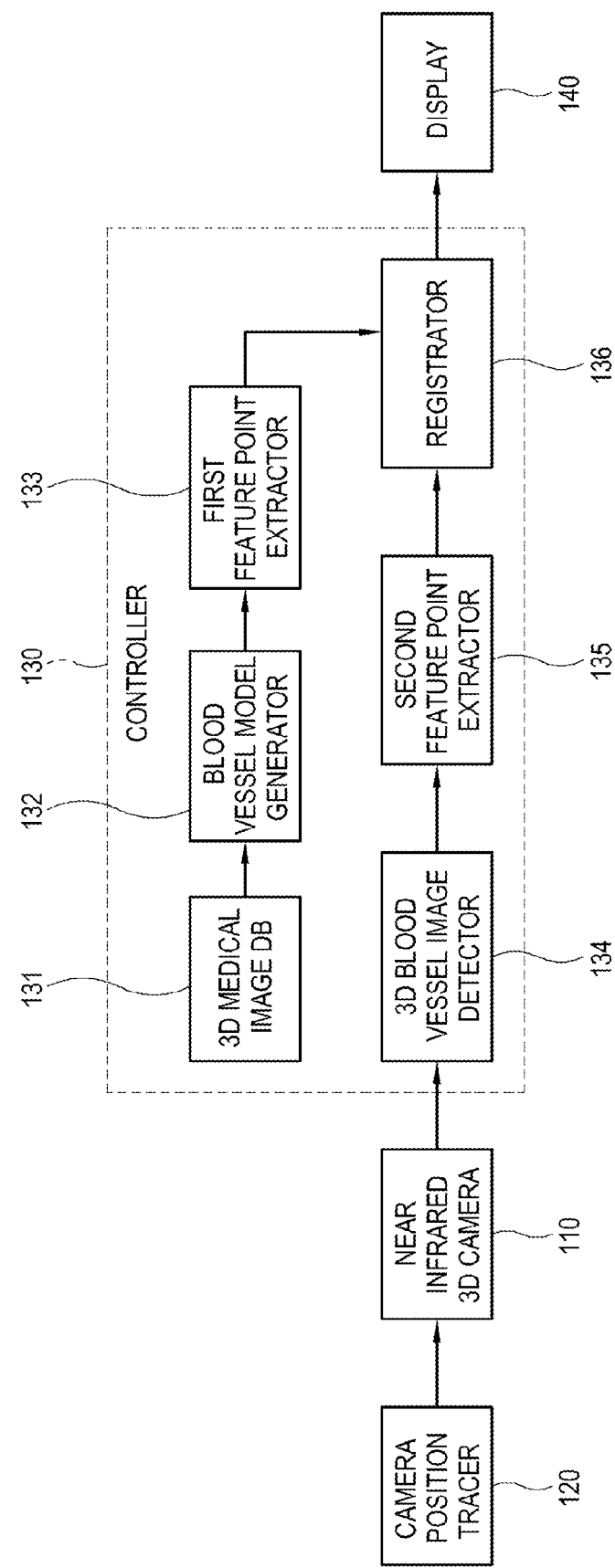
FIG. 1 is a block diagram showing a functional configuration of a system for non-invasive registration between a patient and a 3D medical image according to an exemplary embodiment.

Hereinafter, exemplary embodiments according to the present invention will be described in detail with reference to accompanying drawings. Prior to this, terms or words used in this specification and claims have to be interpreted as the meaning and concept adaptive to the technical idea of the present invention rather than typical or dictionary interpretation on a principle that an inventor is allowed to properly define the concept of the terms in order to explain his/her own invention in the best way.

Therefore, because embodiments disclosed in this specification and configurations illustrated in the drawings are nothing but preferred examples of the present invention and do not fully describe the technical idea of the present invention, it will be appreciated that there are various equivalents and alterations replacing them at the filing date of the present application.

In minimally invasive surgery, a three-dimensional (3D) medical image (computer tomography (CT), a magnetic resonance imaging (MRI), etc.) of a patient is indispensably used for a diagnosis and a surgical plan, and relative position between an intraoperative patient and the 3D medical image is necessary for surgery navigation and surgery guide. Accordingly, an exemplary embodiment provides technology of non-invasive and high precision registration between a patient and the medical image.

Figure 2:
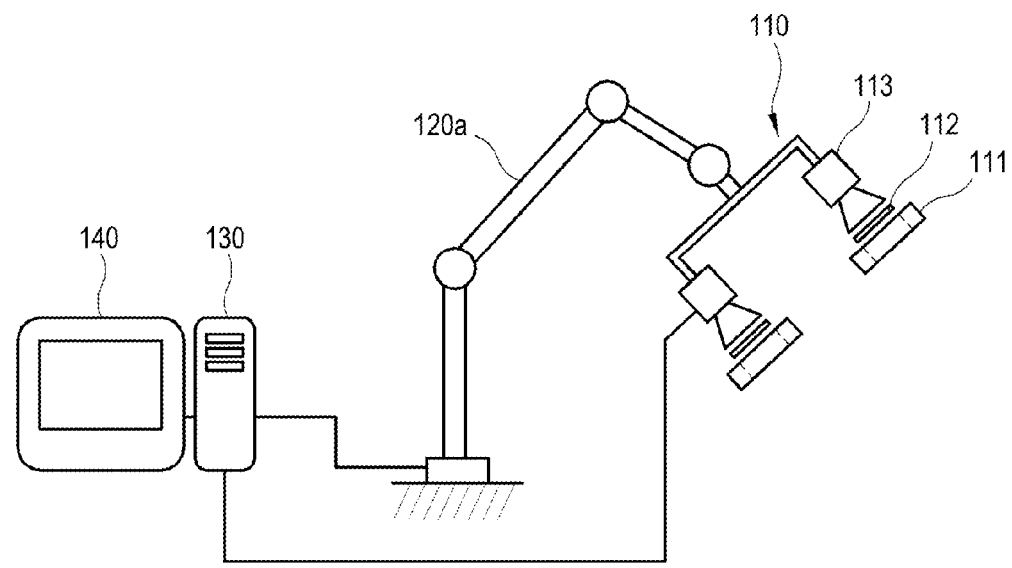
FIG. 2 is a schematic view showing the configuration of the system for non-invasive registration between a patient and a 3D medical image according to an exemplary embodiment.
Figure 2:
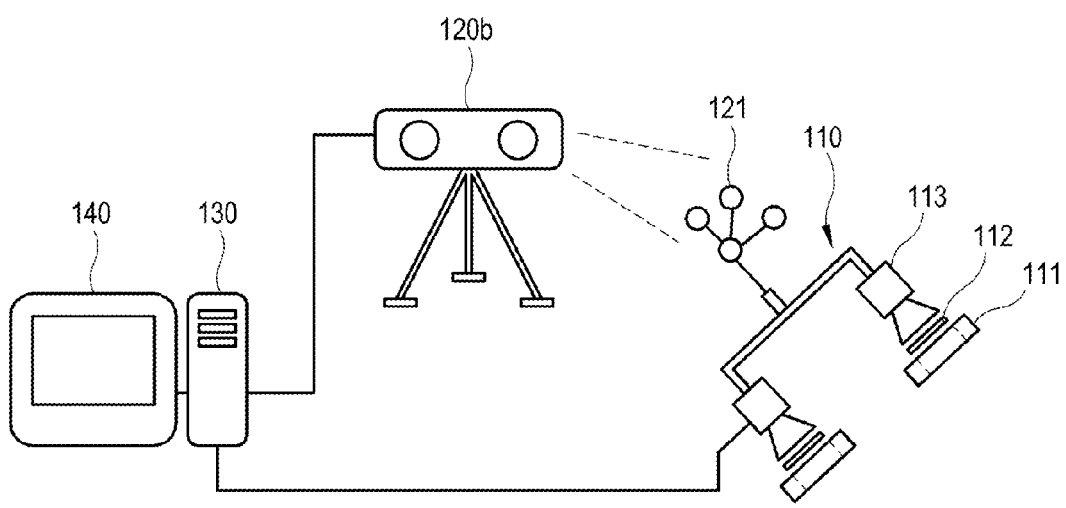

The system for the non-invasive registration between a patient and a 3D medical image according to an exemplary embodiment (hereinafter, referred to as an 'image registration system') is to align a patient's 3D medical image with the patient by a non-invasive method that does not use an artificial fiducial marker but use a feature point based on a blood vessel pattern, in which a patient's blood vessel is extended. As shown in FIGS. 1 and 2, the image registration system includes a near infrared 3D camera 110, a camera position tracer 120, a controller 130 and a display 140.

The near infrared 3D camera 110 is an image taking means to take an image for extracting a 3D blood vessel image I2 of a patient's registration target area during a surgical operation. As shown in FIG. 2, the near infrared 3D camera 110 includes a near infrared light source 111, an LP filter 112 and, a unit camera 113.

Here, the registration target area is a body part taken by each image taking means for position registration between a patient and the 3D medical image I1. The registration target area may be any position as long as it is a part of a patient's body, of which a blood vessel is seen through using the near infrared light, in addition to a surgical part to which a surgical operation is applied.

The near infrared light source 111 is a light emitting means that is provided integrally with the near infrared 3D camera 110 or adjacent to the near infrared 3D camera 110 in the form of an independent module, and emits the near infrared light to the registration target area. The near infrared light source 111 emits near infrared light having a centroid wavelength of a wavelength range (e.g., 700 nm to 800 nm) in which a large amount of deoxyhemoglobin in blood flowing inside the blood vessel such as a vein, an artery, etc. absorbs more light than water occupying the most of the body.

Therefore, when the near infrared light source 111 is emitted to the registration target area, a blood vessel image located inside a patient's skin is seen through, thereby having an environment under which the near infrared 3D camera 110 can take the blood vessel image. Although it is not shown, a diffuse filter for diffusing and transmitting the near infrared light may be placed in front of the near infrared light source 111 so that the intensity of the near infrared light emitted from the light source can become uniform. Further, polarizing plates (not shown) orthogonal to each other may be respectively placed in front of the diffuse filter and the LP filter 112, so that reflected light of the near infrared light emitted to the registration target area can be prevented from being reflected and entering the near infrared 3D camera 110.

The LP filter 112 serves to block light of a near infrared range and visible light. Also, the unit camera 113 uses a charge coupled device (CCD) or complementary metal oxide semiconductor (CMOS) sensor to sense and take a blood vessel image seen through the registration target area by the near infrared light. Further, two unit cameras 113 are spaced apart at a predetermined distance in order to extract the 3D blood vessel image I2 having a 3D form, thereby generating two near infrared blood vessel images having parallax.

The camera position tracer 120 is a tracing means to trace the position of the near infrared 3D camera 110 and calculate the real world coordinates of the 3D blood vessel image I2. The camera position tracer 120 is a reference for a real world coordinate system so that the real world coordinates of the image taken by the near infrared 3D camera 110 can be extracted by tracing the position of the near infrared 3D camera 110 in real time.

Here, the camera position tracer 120 is sorted in accordance with methods of tracing the position of the near infrared 3D camera 110. As shown in (a) of FIG. 2, the camera position tracer 120 may be a mechanical position tracing device 120a that is fastened to an end of an articulated link and measures six degrees of freedom in position of the near infrared 3D camera 110 by sensing a physical displacement due to link movement of each join.

Also, as shown in (b) of FIG. 2, the camera position tracer 120 may be an optical position tracing device 120b that uses the 3D camera taking the fiducial marker 121 mounted to the near infrared 3D camera 110 to calculate a 3D position vector and a 3D direction vector of the fiducial marker 121, and thus measures six degrees of freedom in position of the near infrared 3D camera 110.

The measured data about the six degrees of freedom in position of the near infrared 3D camera 110 measured by the camera position tracer 120 is transmitted to the controller 130 and used as raw data needed for transforming second feature points (to be described later) into real world coordinate values.

The controller 130 is an operator that extracts a first blood vessel pattern from the 3D medical image I1 of the registration target area, extracts a second blood vessel pattern from the 3D blood vessel image I2, and performs position registration between the 3D medical image I1 and a patient through the extracted first and second blood vessel patterns. As shown in FIG. 1, the controller 130 includes a 3D medical image DB 131, a blood vessel model generator 132, a first feature point extractor 133, a 3D blood vessel image detector 134, a second feature point extractor 135 and a registrator 136.

The 3D medical image DB 131 is a database that stores the 3D medical image I1 obtained by taking the registration target area before a surgical operation, and the blood vessel model generator 132 reconstitutes the blood vessel model by segmenting the blood vessel image from the 3D medical image I1 stored in the 3D medical image DB 131.

Also, the first feature point extractor 133 detects a skeleton line SL of the blood vessel model generated by the blood vessel model generator 132, extracts a branch point where the blood vessel is branched, and selects each extracted branch point as a first feature point of the first blood vessel pattern.

The 3D blood vessel image detector 134 extracts the 3D blood vessel image I2 by segmenting the blood vessel image from the near infrared 3D image taken by the near infrared 3D camera 110. The second feature point extractor 135 extracts the branch point of a patient's blood vessel during the surgical operation using the 3D blood vessel image I2 extracted by the 3D blood vessel image detector 134 and the real world coordinate system of the 3D blood vessel image I2 measured by the camera position tracer 120, and selects each extracted branch point as a second feature point of the second blood vessel pattern.

The registrator 136 performs registration by best matching a first feature point group P1 including a plurality of first feature points, and a second feature point group P2 including a plurality of second feature points. Here, the number of first feature points and the number of second feature points respectively included in the feature point groups P1 and P2 are determined in consideration of the numbers required to optimally match the feature point groups P1 and P2. That is, if each number of included feature points is insufficient, there is a limit to optimally match the feature point groups P1 and P2. On the other hand, if each number of included feature points is surplus, there is a limit to obtain the respective feature points at the same time. Preferably, at least three feature points may constitute each of the feature point groups P1 and P2

Meanwhile, the first feature point extractor 133 stores 3D coordinates of the first feature point of the first blood vessel pattern selected with respect to the medical image coordinate system. The near infrared 3D camera 110 takes the blood vessel image seen through a patient's registration target area by the near infrared light to get two 3D blood vessel images I2 having parallax. The second feature point extractor 135 selects the second feature point represented with 3D coordinates in the 3D camera coordinate system based on parallax of a corresponding pair of branch points respectively calculated from two 3D blood vessel image I2 of the near infrared 3D camera 110.

Figure 3:
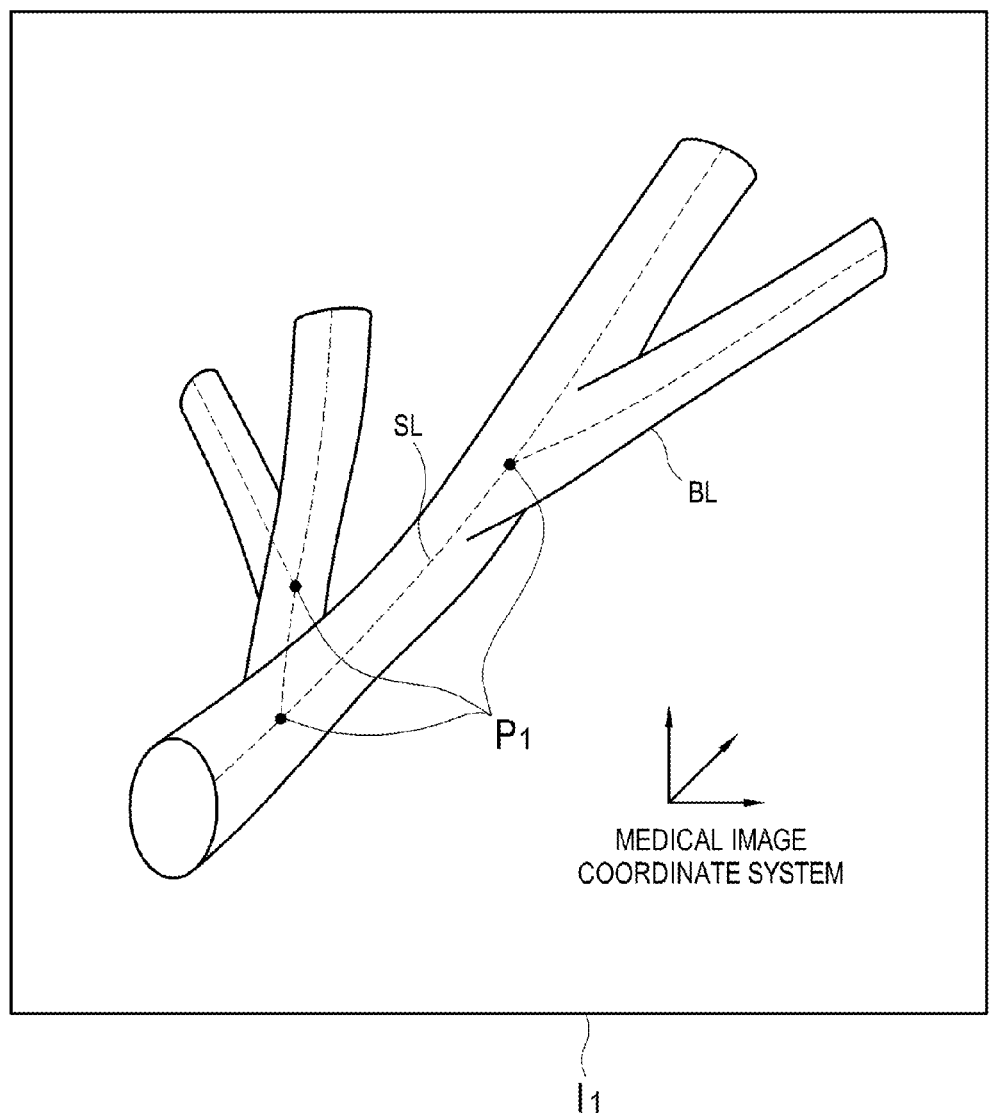
FIG. 3 is a schematic view for explaining a principle of extracting a first feature point group from a 3D medical image according to an exemplary embodiment.

Here, as shown in FIG. 3, the first feature point extractor 133 extracts a bolder line BL representing an outline of the blood vessel in the blood vessel model, and extracts a center line extended from the extracted border line BL along the blood vessel as the skeleton line SL, thereby extracting the skeleton line SL.

Figure 4:
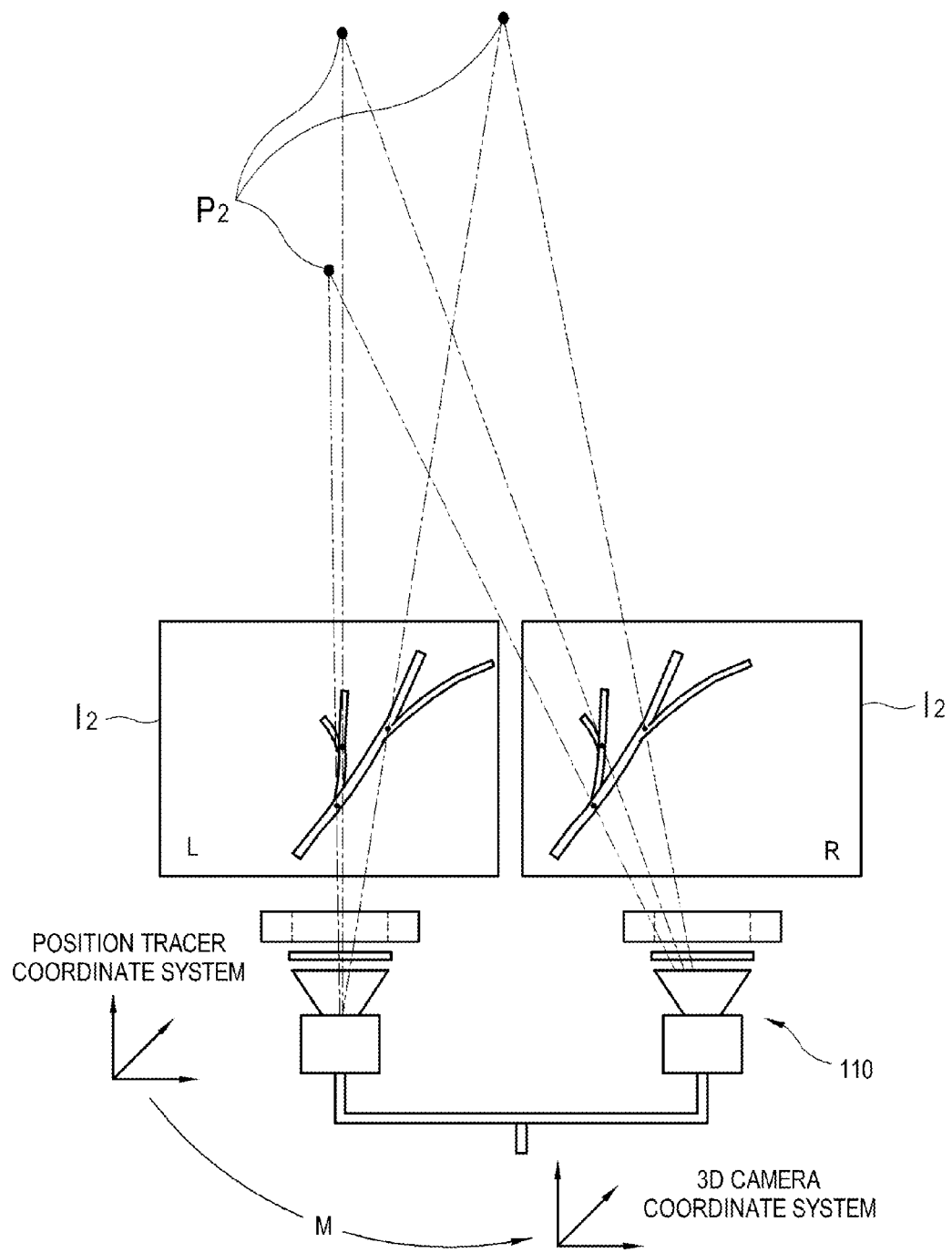
FIG. 4 is a schematic view for explaining a principle of extracting a second feature point group from a 3D blood vessel image according to an exemplary embodiment.
Figure 5:
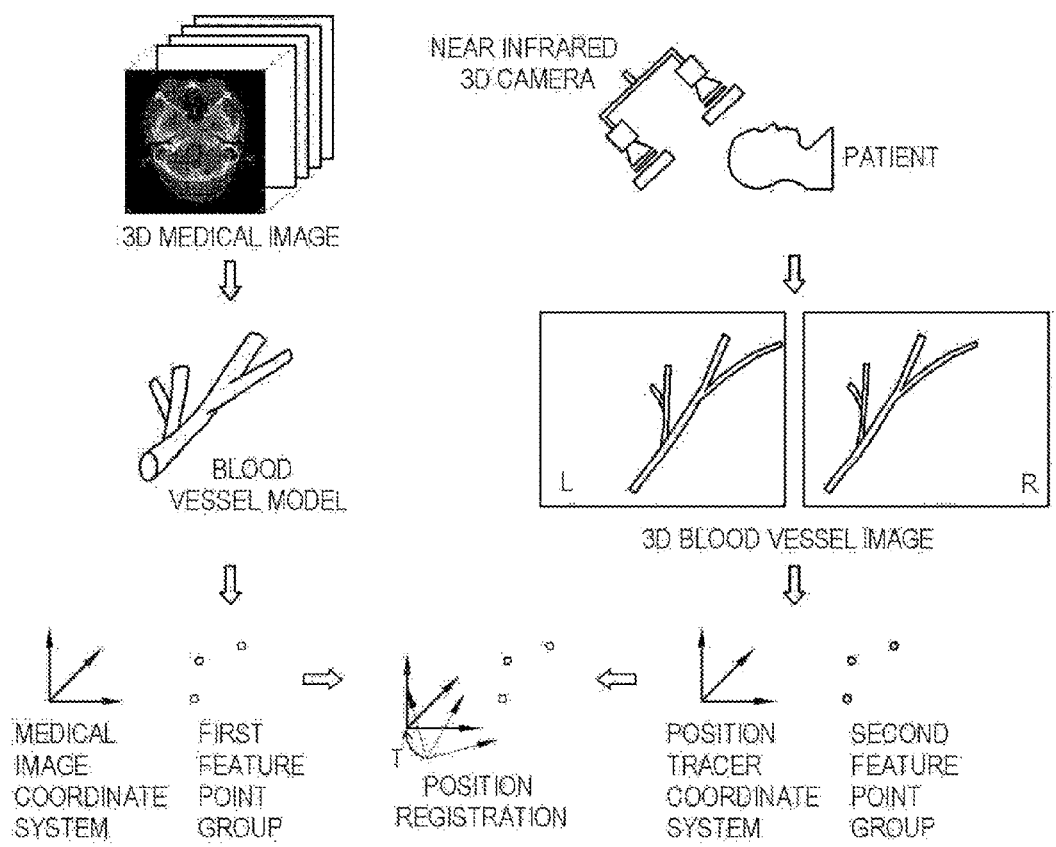
FIG. 5 is a schematic view for explaining a principle of performing registration between a patient and a 3D medical image through the system and method for non-invasive registration between the patient and the 3D medical image according to an exemplary embodiment.

Also, in extracting the second feature point from the 3D blood vessel image I2, like the first feature point extractor 133 as shown in FIG. 4, the second feature point extractor 135 extracts the border line BL representing an outline of the blood vessel image marked in the 3D blood vessel image I2, extracts a center line extended from the extracted border line along the blood vessel as the skeleton line, and selects the branch point, from which each skeleton line is branched, as the second feature point.

Thus, when the feature point according to the blood vessel pattern is extracted from the 3D blood vessel image I2 and the 3D medical image I1, the center line extended along the blood vessel displayed in each image is extracted as the skeleton line, and the branch point of each skeleton line is selected as the feature point, thereby minimizing an error in the border line of the blood vessel, and further reducing a registration error.

In addition, the camera position tracer 120 measures six degrees of freedom in position including three rotation positions and three translation positions about the near infrared 3D camera 110, and tracts the position of the near infrared 3D camera 110 in real time, so that a coordinate transformation matrix M from the position tracer coordinate system to the 3D camera coordinate system can be calculated. At this time, the second feature point extractor 135 transforms the second feature point in the 3D camera coordinate system into that in the position tracer coordinate system by the coordinate transformation matrix M. The registrator 136 rotates and translates the second feature point group P2 of the position tracer coordinate system to optimally match with the first feature point group P1 and thus calculates a position relationship T of the position tracer coordinate system with respect to the medical image coordinate system.

Here, the camera position tracer 120 is fixed to the real world, and thus it is possible to select the position tracer coordinate system to be the real world coordinate system. Since a patient's reference coordinates are involved in the real world coordinate system, the position relationship T is a patient's position relationship with respect to the medical image as a result of a patient-medical image registration.

Meanwhile, the display 140 displays a registration result calculated by the controller 130 in accordance with a control signal of the controller 130 on the screen.

Next, a method of non-invasive registration between a patient and the 3D medical image, using a system for non-invasive registration between a patient and the 3D medical image, will be described according to an exemplary embodiment.

Figure 7:
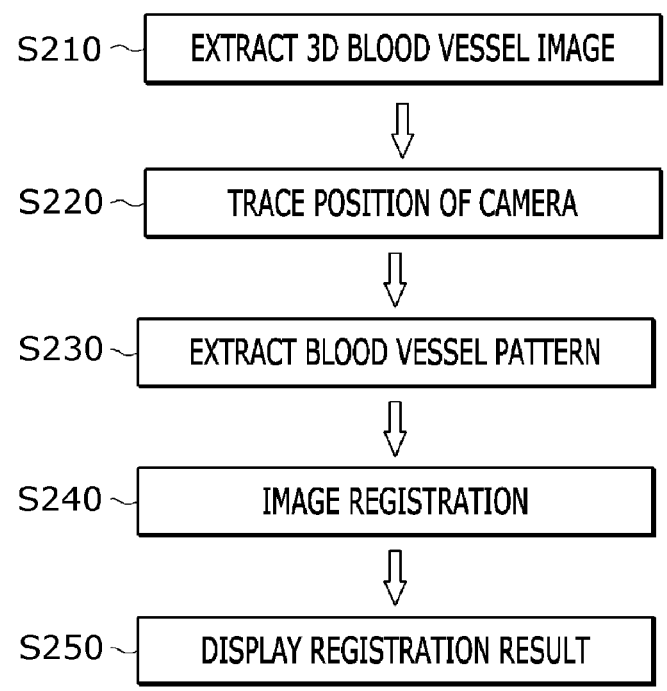
FIG. 7 is a flowchart showing procedure of operations for non-invasive registration between a patient and a 3D medical image according to an exemplary embodiment.

As shown in FIG. 7, the method of non-invasive registration between a patient and the 3D medical image according to an exemplary embodiment includes extracting a 3D blood vessel image (S210), tracing the position of the camera (S220), extracting the blood vessel pattern (S230), image registration S240) and displaying a registration result (S250).

At the operation S210 of extracting the 3D blood vessel image, the near infrared 3D camera 110 takes the blood vessel image seen by having the near infrared light pass through a patient's the registration target area, thereby extracting the 3D blood vessel image I2. At this time, two near infrared blood vessel images having parallax are generated in accordance with distances where two unit cameras 113 provided in the near infrared 3D camera 110 are spaced part from each other, and the generated blood vessel images are transmitted to the controller 130 along a signal line connected to the controller 130.

At the operation S220 of tracing the position of the camera, the camera position tracer 120 traces the position of the near infrared 3D camera 110 in real time to calculate the real world coordinate system for the 3D blood vessel image I2. At this time, the position of the near infrared 3D camera 110 is traced in real time by the camera position tracer 120 such as the mechanical position tracing device 120a, the optical position tracing device 120b, etc., thereby extracting the real world coordinate values of the image taken by the near infrared 3D camera 110. The measured data about six degrees of freedom in position of the near infrared 3D camera 110, measured by the camera position tracer 120 is transmitted to the controller 130 and used as raw data needed for representing the second feature point in the real world coordinate system.

At the operation S230 of extracting the blood vessel pattern, the controller 130 is used to extract the first blood vessel pattern from the 3D medical image I1 of the registration target area and the second blood vessel pattern from the 3D blood vessel image I2. At the operation S240 of image registration, the first blood vessel pattern and the second blood vessel pattern extracted in the operation S230 of extracting the blood vessel pattern are used to perform position registration between the 3D medical image I1 and a patient. Thus, if the blood vessel model generator 132 of the controller 130 separates the blood vessel image from the 3D medical image I1 stored in the 3D medical image DB 131 and reconstitutes the blood vessel model, the first feature point extractor 133 detects the skeleton line SL of the generated blood vessel model and selects each extracted branch point as the first feature point of the first blood vessel pattern.

Also, the 3D blood vessel image detector 134 of the controller 130 extracts the 3D blood vessel image I2 by separating the blood vessel image from the near infrared 3D image transmitted from the near infrared 3D camera 110, and the second feature point extractor 135 extracts the branch point of a patient's blood vessel during the surgical operation through the extracted 3D blood vessel image I2 and the real world coordinate system of the 3D blood vessel image I2 measured by the camera position tracer 120, thereby selecting each extracted branch point as the second feature point of the second blood vessel pattern. At this time, the second feature point extractor 135 transforms the second feature point in the 3D camera coordinate system into that in the position tracer coordinate system through the coordinate transformation matrix M.

Then, the registrator 136 of the controller 130 performs registration by optimally matching the first feature point group P1 that compose of three or more first feature points with the second feature point group P2 that compose of three or more second feature points, in which the second feature point group P2 transformed in the position tracer coordinate system is rotated and translated to optimally match with the first feature point group P1 and then a position relationship T of the position tracer coordinate system is calculated with respect to the medical image coordinate system. In accordance with data about the position relationship T calculated by the registrator 136, the calculated registration result is displayed on the screen of the display 140.

Figure 6:
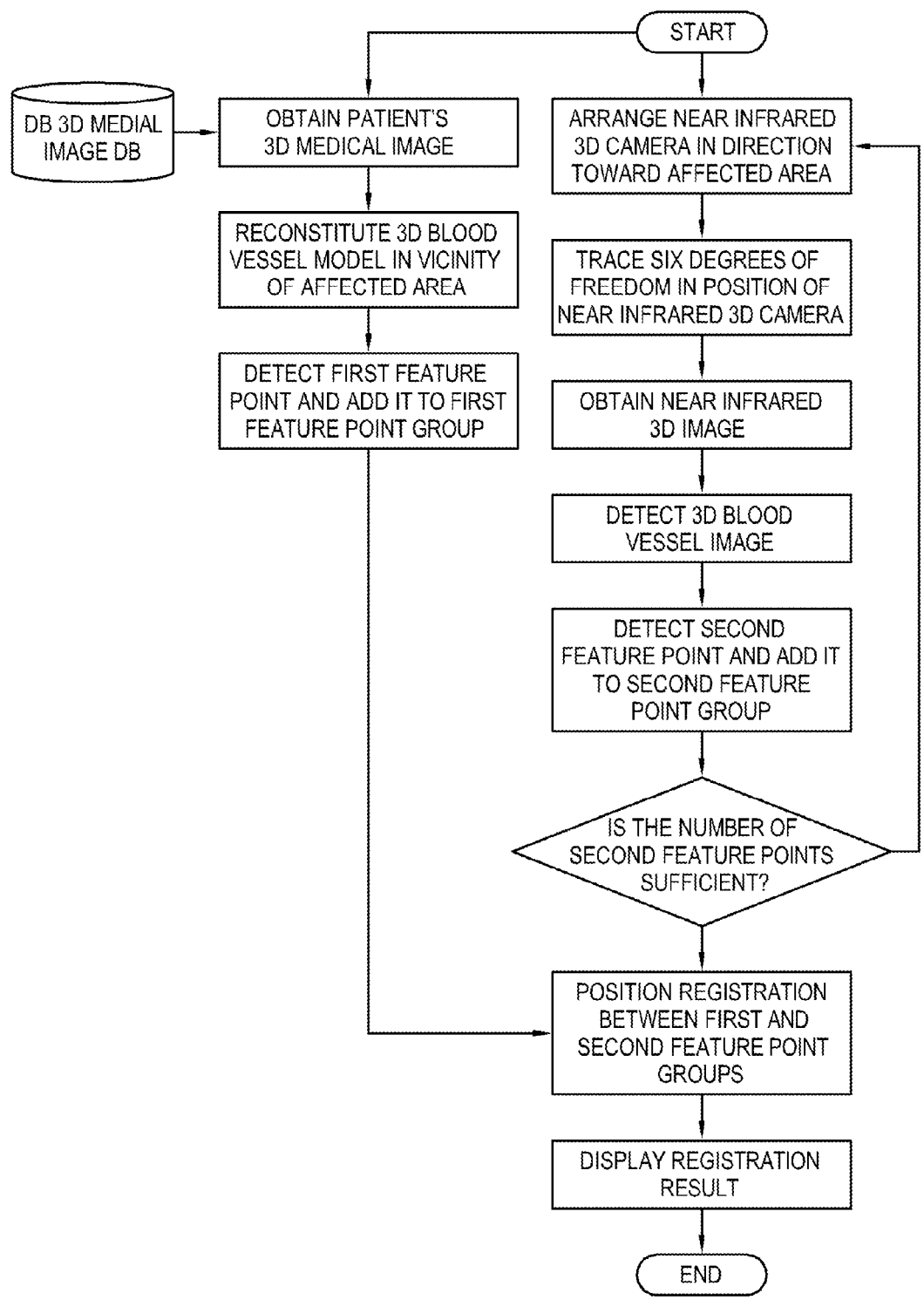
FIG. 6 is a flowchart showing movement procedure of the system for non-invasive registration between a patient and a 3D medical image according to an exemplary embodiment.

Meanwhile, FIG. 6 shows a flowchart of performing the position registration following the system and method for non-invasive registration between a patient and the 3D medical image in accordance with an exemplary embodiment. Referring to FIG. 6, the 3D medical image I1 of the patient is first obtained from the 3D medical image DB 131, and the 3D the blood vessel model is reconstituted with respect to the vicinity of the affected area. Then, the first feature point is extracted from the blood vessel model and additionally stored in the first feature point group P1.

In succession, to register the patient to the medical image during the surgical operation, the near infrared 3D camera 110 is arranged in a direction toward the affected area, and the position of the near infrared 3D camera 110 at this time is traced. Also, when the near infrared 3D image is taken, the 3D blood vessel image I2 is detected, and the second feature point is extracted from the 3D blood vessel image I2, thereby storing it in the second feature point group P2.

At this time, if the number of extracted second feature point is insufficient, the near infrared 3D camera 110 is rearranged to extract the second feature point again and add it to the second feature point group P2.

On the other hand, if number of added second feature points is sufficient, the first feature point group P1 and the second feature point group P2 are registered, and then the registration result is displayed on the display 140.

With the foregoing configuration and functions of the system and method for the non-invasive registration between a patient and the 3D medical image according to an exemplary embodiment, it is possible to non-invasively perform the registration between the patient and the 3D medical image I1 through the position registration between the 3D blood vessel image I2 of the blood vessel arranged in the patient's registration target area obtained using the near infrared light and the blood vessel model included in the 3D medical image I1 obtained by taking the registration target area, without using any fiducial markers.

Also, each blood vessel pattern of the blood vessel images reconstituted from the 3D blood vessel image I2 and the 3D medical image I1 obtained using the near infrared light is analyzed to calculate the feature point for the registration of the branch point of the blood vessel, and thus the registration is performed with respect to the calculated feature point, thereby not only being minimally affected by skin deformation but also reducing an error at the position registration as compared with the conventional registration method using the feature point on a patient's skin.

Furthermore, the position registration is performed based on the feature point according to the blood vessel pattern extended from the blood vessel distributed throughout a human body, thereby being advantageously applicable to various surgical areas and usable as medical information in connection with various medical images.

Although a few exemplary embodiments have been shown and described, it will be appreciated by those skilled in the art that changes may be made in these exemplary embodiments without departing from the principles and spirit of the invention, the scope of which is defined in the appended claims and their equivalents.

What is claimed is:

1. A system for non-invasive registration between a patient and a three-dimensional (3D) medical image, the system comprising:
  a near infrared 3D camera configured to extract a 3D blood vessel image of a patient's registration target area;

a camera position tracer configured to trace a position of the near infrared 3D camera and to calculate a real world coordinate system of the 3D blood vessel image;

a controller comprising:
- a 3D medical image database configured to store a 3D medical image obtained by taking the registration target area;
- a blood vessel model generator configured to reconstitute a blood vessel model by separating a blood vessel image from the 3D medical image;
- a first feature point extractor configured to extract a branch point from which a blood vessel is branched by detecting a skeleton line of the blood vessel model, and to select each extracted branch point as a feature point of a first blood vessel pattern;
- a 3D blood vessel image detector configured to extract a 3D blood vessel image by separating a blood vessel image from a near infrared 3D image taken by the near infrared 3D camera, and a second feature point extractor configured to extract a branch point of a patient's blood vessel through the extracted 3D blood vessel image and a real world coordinate system of the 3D blood vessel image measured by the camera position tracer, and to select each extracted branch point as a feature point of a second blood vessel pattern; and
- a registrator configured to determine a registration result by optimally matching a first feature point group comprising of a plurality of first feature points, and a second feature point group comprising of a plurality of second feature points; and a display configured to display the registration result.

2. The system according to claim 1, wherein
the first feature point extractor further configured to store 3D coordinates of a feature point of a first blood vessel pattern selected with respect to a medical image coordinate system,
the near infrared 3D camera is further configured to take blood vessel images seen by near infrared light through the patient's registration target area to obtain two 3D blood vessel images spaced apart at a distance to have parallax, and
the second feature point extractor is further configure to select a second feature point represented by 3D coordinates with respect to a 3D camera coordinate system, using parallax of a pair of corresponding branch points respectively calculated from two 3D blood vessel images of the near infrared 3D camera.

3. The system according to claim 2, wherein
the camera position tracer is further configured to measure six degrees of freedom in position of the near infrared 3D camera, which comprises three rotation positions and three translation positions, and to calculate a coordinate transformation matrix from the position tracer coordinate system to the 3D camera coordinate system by tracing the position of the near infrared 3D camera in real time,
the second feature point extractor is further configured to transform and to save the second feature point in the 3D camera coordinate system into a position tracer coordinate system by the coordinate transformation matrix, and
the registrator is a non-invasive registration system between patient and 3D medical image, and is further configured to calculate a position relationship of a position tracer coordinate system with respect to a medical image coordinate system in a state that a second feature point group in the position tracer coordinate system is rotated and translated to be optimally matched with the first feature point group.

4. The system according to claim 3, wherein the camera position tracer comprises a mechanical position tracing device which is fastened to an end of an articulated link and is configured to measure six degrees of freedom in position of the near infrared 3D camera by sensing a physical displacement due to link movement of joints.

5. The system according to claim 3, wherein the camera position tracer comprises an optical position tracing device which is configured to use a 3D camera taking fiducial markers mounted to the near infrared 3D camera to calculate a 3D position vector and a 3D direction vector of the fiducial marker and to measure six degrees of freedom in position of the near infrared 3D camera.

6. The system according to claim 1, wherein the first feature point extractor is further configured to extract a border line representing an outline of a blood vessel from the blood vessel model, and to extract a center line, wherein the center line is extracted from the extracted border line along the blood vessel, as the skeleton line.

7. A method of non-invasive registration between a patient and a three-dimensional (3D) medical image, the method comprising:
- extracting a 3D blood vessel image by taking a blood vessel image by passing near infrared light through a registration target area with a near infrared 3D camera;
- tracing a camera position by tracing a position of the near infrared 3D camera in real time with a camera position tracer and calculating a real world coordinate system of the 3D blood vessel image;
- storing a 30 medical image obtained by taking the registration target area;
- reconstituting a blood vessel model by separating a blood vessel image from the 3D medical image;
- extracting a branch point from which a blood vessel is branched by detecting a skeleton line of the blood vessel model;
- selecting each extracted branch point as a feature point of a first blood vessel pattern;
- extracting a 3D blood vessel image by separating a blood vessel image from a near infrared 3D image taken by the near infrared 3D camera;
- extracting a branch point of a patient's blood vessel through the extracted 3D blood vessel image and a real world coordinate system of the 3D blood vessel image measured by the camera position tracer;
- selecting each extracted branch point as a feature point of a second blood vessel pattern,
- determining a registration result by optimally matching a first feature point group comprising of a plurality of first feature points, and a second feature point group comprising of a plurality of second feature points; and
- displaying the registration result on a screen.

* * * * *